cled back to the reactor at a recycle ratio of 0.1:1 to 5:1 mol/mol to fresh feed.

11. The process of claim 4 wherein the reactor column contains vertical, horizontal, or a combination of vertical and horizontal heat exchanger tubes to remove reaction heat and control reaction temperature.

12. The process of claim 11 wherein the heat exchange tubes reduce effective reactor hydraulic diameter, decrease radial and axial mixing in the reactor, and improve reactor efficiency, whereby heat of reaction removal and reactor temperature control are enhanced by controlling feed temperature by heat exchange with reactor effluent and/or a supplemental heater.

13. A process according to claim 4 wherein hydrocarbon gas product is measured to determine propane:propene ratio and reaction severity conditions are adjusted to maintain the propane:propene weight ratio from about 0.2:1 to 50:1.

14. In a process for continuous conversion of ethene-containing light hydrocarbon feedstock to heavier hydrocarbon products wherein the feedstock is contacted with a fluidized bed of zeolite catalyst under conversion conditions, the improvement which comprises passing said feedstock gas consisting essentially of $C_2$ and lighter hydrocarbons upwardly through the fluidized bed in a vertical reactor column having a turbulent reaction zone, while maintaining a superficial velocity in the range from 0.3 to 2 meters per second so that catalyst particles in which the silica:alumina molar ratio is in the range from about 20:1 to about 200:1 are held in a turbulent regime;

maintaining an average density, measured at the bottom of the fluidized bed in the range from about 300 to 500 kg/m$^3$, at a pressure in the range from 410 kPa to 2500 kPa and a temperature in the range from about 315° to 510° C.;

withdrawing a portion of coked catalyst from the reaction zone, oxidatively regenerating the withdrawn catalyst and returning regenerated catalyst to the fluidized bed at a rate sufficient to maintain a reaction severity index, expressed as the propane:propene weight ratio in the hydrocarbon product, in the range from about 0.2:1 to 5:1, whereby at least 70% of ethene feedstock is converted to $C_4+$ hydrocarbons.

15. The process of claim 14 wherein the catalyst comprises a siliceous metallosilicate acid zeolite having the structure of ZSM-5 zeolite and a silica:alumina ratio in the range from about 25:1 to 70:1.

* * * * *

United States Patent [19]

Kocal

[11] Patent Number: 4,746,763

[45] Date of Patent: May 24, 1988

[54] PROCESS FOR PRODUCING AROMATIC COMPOUNDS FROM $C_2$-$C_6$ ALIPHATIC HYDROCARBONS

[75] Inventor: Joseph A. Kocal, Gurnee, Ill.

[73] Assignee: UOP Inc., Des Plaines, Ill.

[21] Appl. No.: 41,279

[22] Filed: Apr. 22, 1987

[51] Int. Cl.$^4$ .................. C07C 2/42; C07C 2/76
[52] U.S. Cl. .................. 585/417; 585/415; 585/418
[58] Field of Search .............. 585/415, 417, 418, 428; 502/71, 77

[56] References Cited

U.S. PATENT DOCUMENTS

| | | | |
|---|---|---|---|
| 3,827,968 | 8/1974 | Givens et al. | 208/49 |
| 3,843,740 | 10/1974 | Mitchell et al. | 585/415 |
| 4,403,044 | 9/1983 | Post et al. | 585/418 |
| 4,467,129 | 8/1984 | Iwayama et al. | 585/481 |
| 4,538,017 | 8/1985 | Butler et al. | 585/415 |
| 4,554,393 | 11/1985 | Lieberts et al. | 585/418 |
| 4,636,483 | 1/1987 | Kjell et al. | 502/71 |
| 4,654,455 | 3/1987 | Chao | 585/415 |

OTHER PUBLICATIONS

European Patent Application No. 0162636, Hall, "Production of Liquid Products from Aliphatic Hydrocarbons", 5-24-84.

Primary Examiner—Patrick P. Garvin
Assistant Examiner—George R. Fourson
Attorney, Agent, or Firm—Thomas K. McBride; John F. Spears, Jr.

[57] ABSTRACT

The present invention relates to a process for producing aromatic compounds from $C_2$-$C_6$ aliphatic hydrocarbons. In this process, a feedstock containing $C_2$-$C_6$ aliphatic hydrocarbons is passed into a reaction zone and into contact with a catalyst zone containing two discrete catalysts. The first catalyst of the discrete catalyst system is comprised in part of a ZSM-5 zeolite component while the second catalyst of the discrete catalyst system is comprised in part of a catalytically active component that is not ZSM-5 which exhibits an acidity lower than that of the first discrete catalyst. A metallic component selected from the Group IIB to IVB Elements of the Periodic Table may be a component of one or both of the discrete catalysts of the instant process as can be a phosphorus-containing alumina component. The discrete catalytic system of the present invention is particularly suited for selectively producing aromatic compounds from $C_2$-$C_6$ aliphatic hydrocarbons while limiting the amount of undesired $C_1$ and $C_2$ by-products produced by the process.

13 Claims, 1 Drawing Sheet

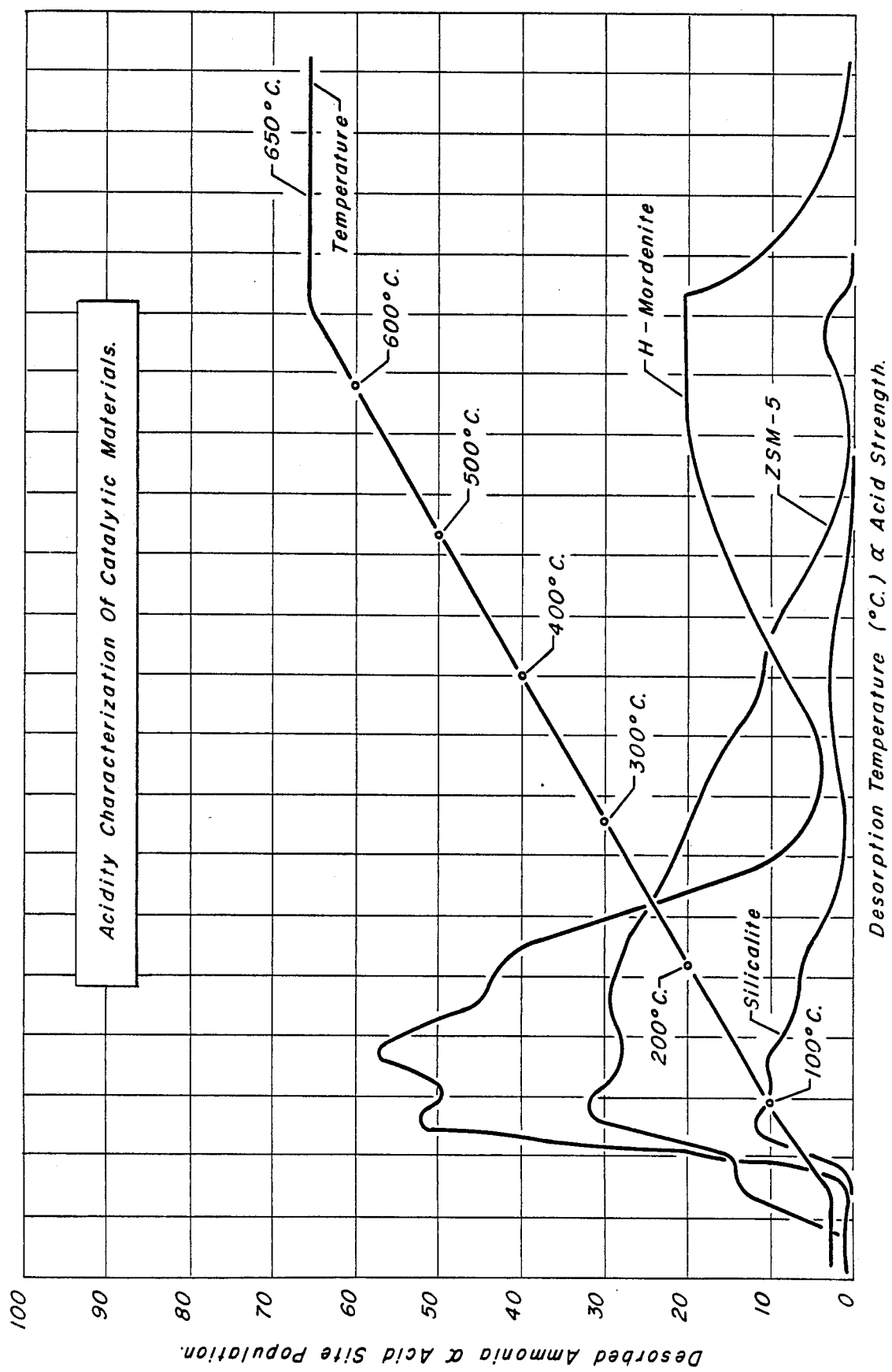

PROCESS FOR PRODUCING AROMATIC COMPOUNDS FROM $C_2$–$C_6$ ALIPHATIC HYDROCARBONS

BACKGROUND OF THE INVENTION

The present invention relates to a process for the production of aromatic hydrocarbons via the dehydrocyclodimerization of $C_2$–$C_6$ aliphatic hydrocarbons by contacting the aliphatic feedstock with a novel mixture of discrete catalysts.

Dehydrocyclodimerization is a process in which reactants comprising paraffins and olefins, containing from 2 to 6 carbon atoms per molecule are reacted over a catalyst to produce primarily aromatics and $H_2$, with a light ends by-product, and a $C_4$+ nonaromatic by-product. This process is distinct from the more conventional reforming or dehydrocyclization processes where $C_6$ and higher carbon number reactants, primarily paraffins and naphthenes, are converted to aromatics. The aromatics produced by dehydrocyclization contain the same or a lesser number of carbon atoms per molecule than the reactants from which they were formed, indicating the absence of reactant dimerization reactions. In contast, the dehydrocyclodimerization reaction results in an aromatic product that almost always contains more carbon atoms per molecule than the $C_2$–$C_6$ reactants, thus indicating that the dimerization reaction is an important step in the dehydrocyclodimerization process. Typically, the dehydrocyclodimerization reaction is carried out at temperatures in excess of 260° C. using dual functional catalysts containing acidic and dehydrogenation components. These catalysts include acidic amorphous aluminas which contain metal promoters. Recently, crystalline aluminosilicates have been successfully employed as catalyst components for the dehydrocyclodimerization reaction. Crystalline aluminosilicates generally referred to as zeolites, may be represented by the empirical formula

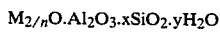

$$M_{2/n}O \cdot Al_2O_3 \cdot xSiO_2 \cdot yH_2O$$

in which n is the valence of M which is generally an element of Group I of II, in particular, sodium, potassium, magnesium, calcium, strontium, or barium and x is generally equal to or greater than 2. Zeolites have skeletal structures which are made up of three dimensional networks of $SiO_4$ and $AlO_4$ tetrahedra, corner linked to each other by shared oxygen atoms. The greater the proportion of the $SiO_4$ species to the $AlO_4$ species, the better suited the zeolite is for use as a component in dehydrocyclodimerization catalysts. Such suitable zeolites include mordenite and the ZSM variety. In addition to the zeolite component, certain metal promoters and inorganic oxide matrices have been included in dehydrocyclodimeriation catalyst formulations. Examples of inorganic oxides include silica, alumina, and mixtures thereof. Metal promoters such as Group VIII or Group III metals of the Periodic Table, have been used to provide the dehydrogenation functionality. The acidic function may be supplied by the inorganic oxide matrix, the zeolite or both.

As stated previously, aromatics, $H_2$, a $C_4$+ nonaromatic by-product, and a light ends by-product are all products of a dehydrocyclodimerization process. Aromatics are a desired product of the reaction. The aromatic compounds produced by the dehydrocyclodimerization process can be utilized as gasoline blending components. A more important use of the aromatic products is in the production of petrochemicals. The aromatic products may be recovered and separated into pure components such as benzene, toluene, xylenes and so forth for use as precursors for polymers, detergents, chemicals, and the like. Hydrogen is also a desirable product of the process. The hydrogen can be efficiently utilized in hydrogen-consuming refinery processes such as hydrotreating hydrocracking processes. The least desirable product of the dehydrocyclodimerization process are the light ends by-products. The light ends byproducts consist primarily of $C_1$ and $C_2$ hydrocarbons produced as a result of the cracking of the $C_2$–$C_6$ aliphatic feed molecules and also as a result of the hydrogenation of ethylene. The suppression of this $C_2$–$C_6$ aliphatic feedstock cracking reaction with a subsequent aromatic product yield increase is the particular object to which this application is directed.

OBJECTS AND EMBODIMENTS

A principal object of this invention is to provide an improved process for the dehydrocyclodimerization of aliphatic hydrocarbons. Further, this improved process results in a reaction which exhibits a higher selectivity towards the production of aromatic hydrocarbons and a lower selectivity towards the production of $C_1$ and $C_2$ by-products thus improving the ability of the process to selectively produce desired aromatic products. Accordingly, a broad embodiment of the present invention is directed toward a dehydrocyclodimerization process employing two discrete catalysts wherein the first discrete catalyst is comprised in part of a ZSM-5 type zeolite component, a phosphorus-containing alumina component, and a metal component selected from the elements of Groups IIB–IVB of the Periodic Table of the Elements. The second discrete catalyst is comprised in part of a catalytically active component that is not ZSM-5 which exhibits an acidity lesser than that of the ZSM-5 complonent of the first discrete catalyst. The second discrete catalyst is also comprised of a phosphorus-containing alumina component. Both catalysts are employed in a dehydrocyclodimerization process under conditions of temperature, pressure, and feed space velocity sufficient to convert a $C_2$–$C_6$ aliphatic feedstock into a product containing aromatic compounds.

In a narrower embodiment, the instant process utilizes from 50 to 95 wt.% of a first discrete catalyst wherein the first discrete catalyst is comprised of a ZSM-5 type aluminosilicate zeolite, from 0.1 to 5 wt.% gallium, and from 40 to 60 wt.% of a phosphorus-containing alumina component. The second discrete catalyst characterized as not being ZSM-5 and of having lesser acidity than the ZSM-5 type aluminosilicate zeolitic component of the first discrete catalyst is preferably comprised of a silicalite component, from 20 to 60 wt.% of a phosphorus-containing alumina component and it may contain from 0.1 to 5 wt.% gallium. The second discrete catalyst is present in the same reaction zone in an amount ranging from 5 to 50 wt.% of the total catalyst loading. Additionally, the phosphorus to alumina ratio of the phosphorus-containing alumina of the first, and second discrete catalyst may range from 1:1 to 1:100. The operating parameters of the process of the instant invention include a temperature range of from 400° to 600° C., a pressure range of from 2 to 10 atmospheres, and a liquid hourly space velocity of from 0.5 to 2.0 hr$^{-1}$. These operating conditions along with a mixture of the first and second discrete catalyst of the instant invention in a reaction zone are sufficient to convert a $C_2$-$C_6$ aliphatic hydrocarbon feed into an aromatic containing product.

These as well as other embodiments of the present invention will become evident from the following, more detailed description.

INFORMATION DISCLOSURE

The prior art recognizes numerous catalyst formulations and processes for the conversion of aliphatic hydrocarbons into aromatic hydrocarbons. Of the processing schemes and catalyst formulations mentioned, none embody all of the aspects of the discrete dual catalytic dehydrocyclodimerization process of the present invention. U.S. Pat. No. 4,636,483 teaches of the use of a gallium modified, aluminum phosphate bound zeolite catalyst for use in a dehydrocyclodimerization process. The catalyst formulation disclosed is identical to that of one of the catalysts of the dual catalytic process of the instant invention, however the '483 patent is silent to the use of a second discrete catalyst for improving the aromatic selectivity of the catalytic process.

Dehydrocyclodimerization and aromatization processes using a dual reactor or a dual catalyst system are disclosed in the prior art. U.S. Pat. No. 3,827,968 disclosed the use of a ZSM-5 based catalyst in a two-reactor system for the aromatization of $C_5^-$ olefins. The catalysts in the two-reactor system are both ZSM-5 based zeolite catalysts but the modification of the ZSM-5 by different means results in two distinct catalytic compounds in separate reactors operating at different conditions to achieve the aromatization of the $C_5^-$ olefins. European Patent EP No. 162636 discloses the use of a more active catalyst and a lesser active catalyst of the same composition where the lesser active catalyst has been deactivated by coke accumulation and where the catalysts are located in two distinct reactors in an aromatization type process. The two disclosures cited immediately above disclose the use of two distinct catalysts comprised of the identical catalytically active component in a two-reactor system. Neither disclosure mentions any advantage to combining the two distinct catalysts in the same reactor, or that catalytic acidity was a factor in selecting the desired catalytic components. These disclosures are also silent to the use of two distinct catalysts with different catalytically active components such as in the process disclosed.

U.S. Pat. No. 4,554,393, discloses the use of a dehydrogenation catalyst in a first reactor, and a crystalline aluminosilica based catalyst in a second reactor for aromatizing paraffins. Again, this disclosure is silent to the combination of the discrete catalysts in a single reactor. U.S. Pat. No. 4,538,017 does however disclose the use of a discrete mixture of a dehydrogenation catalyst and a silicalite containing catalyst for aromatizing paraffins. The invention disclosed in the U.S. Pat. No. 4,538,107 patent varies from that of the instant invention in that the dehydrogenation catalyst must be a metal or metal oxide catalyst and a catalyst such as this could not comprise a discrete catalyst of the instant invention.

U.S. Pat. No. 4,467,129 discloses the use of a dual catalyst system comprising a discrete acid type mordenite containing catalyst and a discrete acid type zeolite catalyst. However, the catalytic mixture is disclosed as being useful only in a process for the dealkylation of ethylbenzene, and no mention is made of basing the choice of zeolites employed in the process upon the acidity characteristics of the zeolites.

U.S. Pat. No. 3,843,740 discloses the use of a two-catalyst bed system. The catalyst of the first bed is comprised of ZSM-5 synthetic aluminosilicate molecular sieve zeolite. The catalyst of the second catalytic bed is a mixture of the first ZSM-5 catalyst and a second molecular sieve catalyst with pore sizes ranging from 4.5 to 6.7 angstroms. The catalytic combination claimed in the U.S. Pat. No. 3,843,740 patent claims superiority to a mixture of both catalysts in both reactors or a reactor system with the two catalysts being contained in separate beds. This disclosure is distinguished from the instant invention in that the instant dual discrete catalyst system disclosed herein is optimally utilized in an intimate admixture, or in a plurality of distinct beds or as distinct catalysts in distinct reactors.

In summation, the prior art does describe the use of a single zeolite, gallium, aluminum phosphate catalyst in a dehydrocyclodimerization process. Additionally, dual reactor process containing distinct catalysts, and single reactor systems containing discrete mixtures of catalysts are disclosed in the prior art. However, none of the prior art is cognizant of the use of a dual, discrete catalytic system where the primary component of the first discrete catalyst exhibits a higher acidity than the primary catalytic component of the second discrete catalyst, nor has any prior art disclosure revealed the utility of the use of such a dual discrete catalytic system to increase the aromatic selectivity of a dehydrocyclodimerization process.

DETAILED DESCRIPTION OF THE INVENTION

This invention is concerned with the dehydrocyclodimerization of aliphatic hydrocarbons utilizing a novel catalytic process comprising a first discrete catalyst comprising a crystalline aluminosilicate zeolite, and a second discrete catalyst comprising a catalytically active component of lesser acidity than the crystalline aluminosilicate component of the first discrete catalyst. It has been surprisingly and unexpectedly found that the dual catalytic process of the instant invention exhibits a higher aromatic selectivity and lower $C_1$ and $C_2$ hydrocarbon selectivity than a conventional single catalyst dehydrocyclodimerization processes. This higher aromatic selectivity increases the yield of desired aromatic reaction products and consequently improves the efficiency and economic attractiveness of the process.

The conversion of paraffins and olefins to aromatic hydrocarbons may be expressed in terms of a three-stage process involving dehydrogenation, oligomerization, and aromatization reactions. While the reaction stages will herein be described as occurring sequentially, it is to be understood that all three reactions will take place simultaneously within the reaction zone. The first reaction stage involves the dehydrogenation of paraffins to form olefins. Olefins may be derived from paraffins by the direct dehydrogenation of a paraffin to form the corresponding olefin and hydrogen or by carbon-carbon fission to produce lower alkanes and olefins. At temperatures thermodynamically favoring dehydrogenation, i.e., temperatures of about 500°-700° C., the direct dehydrogenation reaction competes with the carbon to carbon fission reaction. At these temperatures and in the absence of a dehydrogenation catalyst, the predominant mechanism is fission of the carbon to carbon bond (C—C) which has a lower bond energy than the carbon-hydrogen bond (C—H). The higher the alkane, the greater the tendency toward carbon-carbon fission. In the case of propane, two decomposition reactions are possible, one leading to propylene and free hydrogen the other to ethylene and methane, with the latter slightly predominating. In the case of butane, the predominant reaction is fission at the end of the carbon chain to produce propylene and methane with the next predominant reaction being fission of the interior carbon atoms to produce ethane and ethylene. Only a minor amount of direct dehydrogenation resulting in butenes and free hydrogen takes place.

Ethylene, ethane, and methane are the least desirable products of the carbon fission reaction. Methane remains in the reactor system as a refractory product. In a desired reaction, ethane may be dehydrogenated to ethylene prior to oligomerization to larger hydrocarbons. This reaction however occurs slowly and due to the speed and frequency of the undesirable ethylene hydrogenation reaction, the dehydrogenation reaction does not substantially alter the ethane concentration in the reaction mixture. In fact, the concentration of ethane in the reaction mixture will increase with increasing reactor residence time due to the dominance of the ethylene hydrogenation reaction in comparison to the ethylene oligomerization or ethane dehydrogenation reactions. The ethylene carbon fusion reaction product as previously explained may be hydrogenated to ethane or oligomerized.

In the second stage of the conversion process, the olefins undergo oligomerization to produce cyclic naphthenes. These naphthenes are then dehydrogenated in the third stage of the conversion process to produce the corresponding aromatic compounds. The cyclic naphthenes include saturated cycloalkanes and unsaturated alicyclic compounds with the former usually predominating. The predominant cyclic naphthenes produced in the second stage are six-member cyclic rings substituted with one or two alkyl groups containing a total of 1 to 12 carbon atoms. These cyclic naphthenes are dehydrogenated to produce the corresponding aromatic hydrocarbons, e.g. benzene, toluene, ethylbenzene, xylenes, and other alkyltoluenes.

To maximize the production of aromatics in a dehydrocyclodimerization process, the amounts of methane and ethane produced by the dehydrocyclodimerization process must be minimized. The addition of a second discrete catalyst containing an active component not the same as and exhibiting lesser acidity than that of the first discrete catalyst of the instant invention succeeds in reducing the amount of these undesired products produced in a dehydrocyclodimerization process. This result is explained by first reviewing the catalytic functions of the different components of the discrete catalysts disclosed herein. The acidic component of the catalysts promotes the cracking or carbon fission reaction. Additionally, the acidic components catalyze the hydrogenation reactions taking place in the process. Metal modifiers such as gallium, indium, or rhenium attenuate the strength of the acidic sites of the catalysts and they also promote the dehydrogenation reaction. The lesser acidic catalyst tends to assist in the catalyzing of the oligomerization reactions among others.

In reviewing the catalytic functions of the components of the catalysts of the instant invention, it can be seen that the dual discrete catalytic system of the present invention is able to increase the aromatic selectivity of a dehydrocyclodimerization process by: (1) slowing the rate of the carbon fission reaction and ethylene hydrogenation reaction by reducing the average acidity of the dual catalyst system while maintaining a substantial amount of strong acid sites, and (2) promoting the oligomerization of ethylenes as opposed to the hydrogenation of ethylenes by increasing the rate that the ethylene oligomerization reaction takes place in comparison to the ethylene hydrogenation reaction.

The characterization of the acidity of active catalytic components is an important aspect of the instant invention. The acidity of catalytic components is a function of the number and strength of acidic sites on a catalyst. In the case of a crystalline aluminosilicate zeolite material, acidity is directly related to the charge difference between the silica and alumina constituents of the crystalline structure. In fact, acidity is directly related to the silica/alumina ratio of a zeoliticmaterial with zeolites having a high alumina content exhibiting a high acidity. This particular property of aluminosilicate zeolites gives them ion exchange properties making them good adsorbents, and also gives them excellent hydrocarbon cracking properties.

The acidity of a zeolitic material may be measured using a variety of analytical techniques. Some of these techniques include traditional titration methods, microcalorimetry, fluorescent titration, infrared spectroscopy, and temperature programmed desorption of ammonia. While any one of these methods may be utilized to determine catalytic acidity, it is felt that temperature programmed desorption of ammonia provides the most reliable and reproducible method of characterizing catalytic acidity. In the temperature programmed desorption of ammonia, ammonia acts as a probe molecule becoming stabilized upon acid sites on the surface and within the smallest pores of a catalyst. The ammonia is then desorbed from the acid sites by programmed heating of the catalyst sample. The amount of ammonia being liberated is measured continuously with the weaker acidic sites releasing the ammonia at low temperatures, and the stronger acidic sites releasing the ammonia at increasingly higher temperatures. The ammonia desorption curve is used to determine total acidity and therefore may be used as a basis for catalyst acidity comparison. Regardless of the analytical technique used, it is emphasized that the same technique should be used for all samples when determining the relative acidities of the two catalysts utilized in the instant invention.

The dual catalytic system employed in the dehydrocyclodimerization process of the present invention is characterized in that the first discrete catalyst comprises a ZSM-5 type crystalline aluminosilicate zeolite, and the second discrete catalyst comprises a catalytically active component that is not ZSM-5 and that exhibits an acidity lower than the ZSM-5 crystalline aluminosilicate zeolite of the first discrete catalyst. Both discrete catalysts comprise a phosphorus-containing alumina component, and both may comprise a metal component selected from the elements of Groups IIB–IVB of the Periodic Table of the Elements. The phosphorus may be incorporated with the alumina in any acceptable manner known to those skilled in the art. Examples of such incorporation techniques include pillings, nodulizing, marumerization, spray drying, extrusion, or any combination of these techniques. One preferred method of preparing this phosphorus-containing alumina is the gelation of a hydrosol precursor in accordance with the well-known oil drop method. A phosphorus compound is added to an alumina hydrosol to form a phosphorus-containing alumina hydrosol. Representative phosphorus-containing compounds which may be utilized in the present invention include: $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical, and X is hydrogen, R, or a halide. These compounds include primary, $RPH_2$, secondary, $R_2PH$ and tertiary, $R_3P$ phosphines such as butyl phosphine, and tertiary phosphine oxides $R_3PO$, such as tributyl-phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkyl-phosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof, such as the monopropyl ester, alkyl dialkylphosphinites, $(RO)PR_2$ and dialkyl alkylphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contin one to four carbon atoms.

Other suitable phosphorus-containing compounds include ammonium hydrogen phosphate, the phosphorus halides such as phosphorus trichloride, bromide, and iodide, alkylphosphorodichloridites, $(RO)PCl_2$, dialkyl-phosphorochloridites, $(RO)_2PCl$, dialkylphosphinochloridites, $R_2PCl$, alkyl alkylphosphonochloridates, $(RO)(R)P(O)Cl$, dialkylphosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

The amount of phosphorus in the resultant catalytic composite can vary over a wide range. A phosphorus to aluminum molar ratio ranging from about 1:1 to about 1:100 is preferred. The 1:1 molar ratio corresponds to a phosphorus-containing alumina containing 24.7 wt.% aluminum and 20.% wt.% phosphorus, while the 1:100 molar ratio corresponds to 0.6 wt.% phosphorus and 52.0 wt.% aluminum.

The alumina hydrosol is typically prepared by digesting aluminum in aqueous hydrochloric acid and/or aluminum chloride solution at about reflux temperature, usually from about 80° to about 105° C., and reducing the chloride compound concentration of the resulting aluminum chloride solution by the device of maintaining an excess of the aluminum reactant in the reaction mixture as a neutralizing agent. The alumina hydrosol is an aluminum chloride hydrosol variously referred to an an aluminum oxychloride hydroxol, aluminum hydroxychloride hydrosol, and the like, such as is formed when utilizing aluminum metal as a neutralizing agent in conjunction with an aqueous aluminum chloride solution. In any case, the aluminum chloride is prepared to contain aluminum in from about a 0.70:1 to about 1.5:1 weight ratio with the chloride compound content thereof.

In accordance with one embodiment of the invention, a phosphorus-containing alumina is prepared by a method which comprises admixing the alumina hydrosol with a phosphorus-containing compound, the phosphorus to aluminum molar ratio in the resulting phosphorus-containing admixture being from 1:1 to 1:100 on an elemental basis and subsequently mixing in the ZSM-5 crystalline aluminosilicate of the first discrete catalyst or the non-ZSM-5 active catalytic component of the second discrete catalyst and then gelling said admixture to obtain said catalyst composite of phosphorus-containing alumina.

In one specific embodiment, the phosphorus compound is mixed with a gelling agent before admixing with the alumina hydrosol. It is preferred that said alumina hydrosol contain the active catalytic component of the first or second discrete catalyst. Commingling of the alumina hydrosol, containing said active catalytic component, with the phosphorus-gelling agent mixture is effected by any suitable means. The resultant admixture is dispersed as droplets in a suspending medium under conditions effective to transfrom said droplets into hydrogel particles.

The gelling agent is typically a weak base which, when mixed with the hydrosol, will cause the mixture to set to a gel within a reasonable time. In this type of operation, the hydrosol is typically coagulated by utilizing ammonia as a neutralizing or setting agent. Usually, the ammonia is furnished by an ammonia precursor which is added to the hydrosol. The precursor is suitably hexamethylenetetramine, or urea, or mixtures thereof, although other weakly basic materials which are substantially stable at normal temperatures, but decompose to form ammonia with increasing temperature, may be suitably employed. It has been found that equal volumes of the hydrosol and of the hexamethylenetetramine solution to alumina sol solution are satisfactory, but it is understood that this may vary somewhat. The use of a smaller amount of hexamethylenetetramine solution tends to result in soft spheres while, on the other hand, the use of larger volumes of base solution results in spheres which tend to crack easily. Only a fraction of the ammonia precursor is hydrolyzed or decomposed in the relatively short period during which initial gelation occurs.

An aging process is preferably subsequently employed. During the aging process, the residual ammonia precursor retained in the spheroidal particles continues to hydrolyze and effect further polymerization of the hydrogel whereby desirable pore characteristics are established. Aging of the hydrogel is suitably accomplished over a period of from about 1 to about 24 hours, preferably in the oil suspending medium, at a temperature of from about 60° to about 150° C. or more, and at a pressure to maintain the water content of the hydrogel spheres in a substantially liquid phase. The aging of the hydrogel can also be carried out in aqueous $NH_3$ solution at about 95° C. for a period up to about 6 hours. Following the aging step, the hydrogel spheres may be washed with water containing ammonia.

The phosphorus-containing alumina component of the two discrete catalysts of the present invention may also contain minor proportions of other well-known inorganic oxides such as silica, titanium dioxide, zirconium dioxide, tin oxide, germanium oxide, chromium oxide, beryllium oxide, vanadium oxide, cesium oxide, hafnium oxide, zinc oxide, iron oxide, cobalt oxide, magnesia, boria, thoria, and the like materials which can be added to the hydrosol prior to dropping.

As mentioned previously, the first and second discrete catalysts of the instant invention both may contain a metal component selected from the elements of Groups IIB-IVB of the Periodic Table of the Elements. This metal component may be present in any form including elemental metal, oxide, hydroxide, halide, oxyhalide, aluminate, or in chemical combination with one or more of the other ingredients of the catalytic composite. Although it is not intended to restrict the present invention by this explanation, it is believed that the best results are obtained when the metal component is present in the composite in the zero valency state. This metal component can be used in any amount which is catalytically effective with good results obtained, on an elemental basis, with about 0.1 to about 5% of the metal component by weight of the total catalytic composite. Best results are ordinarily achieved with about 0.5 to 1 wt.% of the metal component, calculated on an elemental basis. Although not a necessary condition of the present invention, it is believed that a substantial portion of the metal present in the catalyst composite is located in and/or on the active catalytic component of the discrete catalysts. It is a preferred embodiment of the present invention that when present in either discrete catalyst that the Group IIB-IVB metal component comprise gallium.

The optional gallium component may be incorporated in the catalytic composite in any suitable manner known to the art to result in a relatively uniform dispersion of the gallium, such as, by ion exchange, cogelation, or impregnation either after, before, or during the compositing of the catalyst formulation. Additionally, the gallium component of the first and/or second discrete catalyst may be surface impregnated such that the majority of the gallium is located on the outer portion of the catalyst particle, by means such as a low acid impregnation, by chemical complexing, or by pore blockage prior to impregnation of the gallium. It is to be noted that it is intended to include within the scope of the present invention all conventional methods for incorporating and simultaneously distributing either uniformly or non-uniformly a metallic component in a catalytic composite and the particular method of incorporation used is not deemed to be an essential feature of the present invention. A preferred method of incorporating the gallium involves ion exchange of the active catalytic component with a soluble, decomposable compound of gallium, such as, gallium tribromide, gallium perchlorate, gallium trichloride, gallium hydroxide, gallium nitrates, gallium oxalate, and the like compounds.

The first discrete catalyst of the instant invention is characterized as comprising in part a crystalline aluminosilicate zeolite. In particular, a family of crystalline aluminosilicates are preferred, specifically those with silica to alumina ratios of at least 12. A particularly preferred family is the one identified as the ZSM variety. Included among this ZSM-5, ZSM-8, ZSM-11, ZSM-12, ZSM35, and other similarly behaving zeolites. It is most preferred that ZSM-5 be utilized as the crystalline aluminosilicate component of the present invention. These ZSM type zeolites are generally prepared by crystallizing a mixture containing a source of alumina, a source of silica, a sourc of alkali metal, water, and a tetraalkylammonium compound of its precursors. Of course, other crystalline aluminosilicates which meet the silica to alumina ratio criteria may be used, such as, faujasites, L-type, mordenites, omega-type, and the like. The relative proportions of the crystalline aluminosilicate zeolite and the other components of the catalytic composite vary widelyu with the zeolite conent ranging from about 40% to about 80% by weight and more preferably in the range from about 50% to 70% by weight of composite.

The second discrete catalyst of the instant invention is characterized as comprising a catalytically active component not the same as that of the ZSM-5 zeolite of the first discrete catalyst and of lesser acidity than the ZSM-5 zeolite of the first discrete catalyst. The catalytically active component of the second discrete catalyst may therefore be a crystalline aluminosilicate material distinct from that of the first discrete catalyst, a metal oxide material, an amorphous silica-alumina material, a crystalline silica material or any number of catalytically active materials that have been disclosed in the prior art, and which exhibit an acidity as measured by a previously disclosed acidity determination method lower than that of the first discrete catalyst. By "catalytically active component", it is meant a component that has been shown to allow a chemical reaction to occur, or one which accelerates a chemical reaction without being consumed therein. It is most preferred that silicalite be utilized as the active catalytic component of the second discrete catalyst. Silicalite is a hydrophobic crystalline silica molecular sieve. Silicalite is disclosed and claimed in U.S. Pat. Nos. 4,061,724 and 4,104,294 to Grose et al, incorporated herein by reference. Silicalite differs from zeolites in that silicalite does not exhibit appreciable ion exchange properties as $AlO_4$ tetrahedra do not comprise a portion of the crystalline silica framework. However, alumina does exist in silicalite as an impurity. Commercially available silica sols can typically contain from 500 to 700 ppm $Al_2O_3$. It is the presence of this small amount of alumina that imparts a slight acidity to silicalite and gives it surprising utility as the less acidic active catalytic component of the second discrete catalyst.

The first and second discrete catalytic composites of the instant invention may be shaped into any useful form, such as, spheres, pills, cakes, extrudates, powders, granules, tablets, etc., and utilized in any desired size. Formation usually occurs during the compositing of the catalytic components, following any known method in the art. For the purposes of the present invention, a particular useful shape of the subject catalytic composite is the sphere, manufactured by the well-known oil drop method which in the case of ZSM-5 zeolite containing first discrete catalyst comprises: forming an alumina hydrosol by any of the techniques taught in the art and preferably by reacting aluminum metal with hydrochloric acid, and combining the resultant hydrosol with the crystalline aluminosilicate zeolite. This alumina zeolite hydrosol is commingled with a suitable gelling agent which has been contacted with a phosphorus-containing compound as previously set forth hereinabove. The resultant admixture is then ready for forming. In the case of the second discrete catalyst of the instant invention comprising a catalytically active component of lesser acidity than and not the same as the ZSM-5 zeolite of the first discrete catalyst, the catalyst preparation procedure comprises: forming an alumina hydrosol by any of the techniques taught in the art and preferably by reacting aluminum metal with hydrochloric acid, combining the resultant hydrosol with the desired active catalytic component which, in the case of silicalite, would be a colloidal silica solution. This alumina-silicalite hydrosol is commingled with a suitable gelling agent which has been contacted with a phosphorus-containing compound as previously set forth hereinabove. The resultant admixture is then ready for forming.

To form the first and second discrete catalyst composites of the instant invention, the forming solutions of the discrete catalysts are separately dispersed as droplets into an oil bath maintained at elevated temperatures. The droplets of each mixture remain in the oil bath until they coagulate and form hydrogel spheres. The spheres are continuously withdrawn from the oil bath and typically subjected to specific aging treatments in oil and an ammoniacal solution to further improve their physical characteristics. The resulting aged and gelled particles are then washed and dried at a relatively low temperature of about 150° to about 205° C. and subjected to a calcination procedure at a temperature of about 450° to about 700° C. for a period of about 1 to about 20 hours. This treatment effects conversion of the hydrogel spheres to the desired phosphorus-containing alumina composite. See the teachings of U.S. Pat. No. 2,620,314 for additional details.

The dehydrocyclodimerization conditions which will be employed for use with the dual discrete catalyst composition of the present invention will, of course, vary depending on such factors as feedstock composition and desired conversion. A desired range of conditions for the dehydrocyclodimerization of $C_2$–$C_6$ aliphatic hydrocarbons to aromatics include a temperature from about 350° to about 650° C., a pressure from about 1 to about 20 atmospheres, and a liquid hourly space velocity from about 0.2 to about 5 $hr^{-1}$. The preferred process conditions are a temperature in the range from about 400° C. to about 550° C., a pressure in or about the range from 2 to 10 atmospheres, and a liquid hourly space velocity of between 0.5 and 2 $hr^{-1}$. It is understood that, as the average carbon number of the feed increases, a temperature in the lower end of temperature range is required for optimum performance and conversely, as the average carbon number of the feed decreases, the higher the required reaction temperature.

The feed stream to the dehydrocyclodimerization process is defined herein as those streams introduced into the dehydrocyclodimerization reaction zone which provide reactants for the three dehydrocyclodimerization reactions mentioned hereinabove. Included in the feed stream are $C_2$–$C_6$ aliphatic hydrocarbons. By $C_2$–$C_6$ aliphatic hydrocarbons is meant that the feed stream may comprise one or more open, straight or branched chain isomers having from about 2 to 6 carbon atoms per molecule. Furthermore, the hydrocarbons in the feedstock may be saturated or unsaturated. Preferably, the hydrocarbons $C_3$ and/or $C_4$ are selected from isobutane, normal butane, isobutene, normal butene, propane, and propylene. Diluents, refractory or reactant in nature, may also be included in the feed stream. Examples of such diluents include hydrogen, nitrogen, helium, argon, neon, CO, $CO_2$, $H_2O$ or its precursors. Water precursors are defined as those compounds which liberate $H_2O$ when heated to dehydrocyclodimerization reaction temperatures. Methane and hydrocarbons greater than $C_6$ aliphatic hydrocarbons may also be components of the feedstock of the instant invention. These components will generally be refractory reactants but it is expected that the inclusion of such components in the feed will detrimentally affect the reaction kinetics of the instant process.

It is anticipated that the $C_2$–$C_6$ aliphatic hydrocarbon feedstream utilized in the process of the instant invention may originate as a product or by-product of a refinery or petrochemical process. The light aliphatic hydrocarbons produced and recovered in a cracking or a reforming process would be examples of such process derived feed streams. The products of a synthesis gas production process is another potential source of feed for the instant process. Another anticipated source of feed for the process described herein is the light aliphatic hydrocarbons recovered at the wellhead at oil production facilities.

According to the present invention, the feed stream is contacted with the two discrete catalytic composites of the instant invention in a dehydrocyclodimerization reaction zone maintained at dehydrocyclodimerization conditions. This contacting may be accomplished by using the two catalytic composites in a fixed bed system, a moving bed system, a fluidized bed system, or in a batch-type operation; however, in view of the fact that attrition losses of the valuable catalyst should be minimized and of the well-known operational advantages, it is preferred to use either a fixed bed catalytic system, or a dense phase moving bed system such as is shown in U.S. Pat. No. 3,725,249. It is contemplated in the case a fixed bed catalytic system is employed to accomplish the process of the present invention that the two discrete catalysts of this invention may be uniformly mixed throughout the reaction zone of one or more fixed bed reactors. Alternatively, it is anticipated that the two discrete catalysts may be located in a multiplicity of distinct single catalyst containing layers within a single fixed bed reactor or a plurality of fixed bed reactors. In the case where a multiple bed system is anticipated, the two distinct catalysts may be located in any manner including locating a distinct catalyst alone in a distinct reactor, of locating the catalysts using the methods listed above or a combination of the methods listed above such that both discrete catalysts are utilized inthe reaction zone of the instant process at a weight ratio of the first more acidic discrete catalyst to the second lesser acidic discrete catalyst of from 1:1 to 19:1 on a total catalyst weight basis. In the case where a dense phase moving bed system is used, the two discrete catalysts will most likely be uniformly mixed within the reaction system at weight ratio ranges identical to those listed above.

In a fixed bed system or in a dense-phase moving bed system, the feed stream is preheated by any suitable heating means to the desired reaction temperature and then passed into a dehydrocyclodimerization zone containing a bed of the instant catalytic composite. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, admixed liquid-vapor phase, or a vapor phase when they contact the catalyst, with the best results obtained in the vapor phase. The dehydrocyclodimerization system then preferably comprises a dehydrocyclodimerization zone containing one or more fixed or dense-phase moving beds of the instant catalytic composite.

In a multiple bed system, the dehydrocyclodimerization zone may be one or more separate reactors with suitable heating means therebetween to compensate for any heat loss encountered in each catalyst bed. Specific to the dense-phase moving bed system, it is common practice to remove catalyst from the bottom of the reaction zone, regenerate it by conventional means known to the art, and then return it to the top of the reaction zone.

The reactor or reactors utilized in the instant process may be linked to the product recovery system in various manners described in the prior art to achieve specific desired results. U.S. Pat. No. 4,642,402 for example discloses a method of combining a reaction zone and product recovery zone to optimize the xylene produced in a dehydrocyclodimerization process. Additionally, it is anticipated that the product produced in the reaction zone of the process described herein may be recovered utilizing any method disclosed in the prior art. For instance, U.S. Pat. Nos. 3,537,978 and 3,574,089 describe the recovery of naphtha, hydrogen-rich recycle gas, and light hydrocarbon streams from the effluent of a catalytic reforming zone. U.S. Pat. No. 3,101,261 illustrates a process to recover light ends and naphtha from the effluent of a reforming reaction zone. These references are pertinent for their teaching the use of such separatory techniques as partial condensation, stripping columns, and absorption.

Processing schemes disclosed in the prior art as methods of improving process or separation efficacy are also anticipated as being useful as a portion of the process of the present invention. For example, U.S. Pat. Nos. 4,381,417 and 4,381,418 describe product recovery systems for dehydrogenation processes in which expansion of a gas stream provides fluids used as coolant media. Referring to the latter reference, the reactor effluent is cooled, dried, further cooled, and then passed into a vapor-liquid separation zone 28. The vapors from this zone are depressurized in turbine 32 to yield a cold mixed phase stream collected in separation zone 34. Liquid from this zone is flashed into the separation zone 51.

U.S. Pat. No. 3,838,553 is pertinent for its description of the use of low temperatures and elevated pressures to affect the separation of vapors and for the integration of a low temperature separation zone with a different type of separation zone. In FIG. 2 of this reference, the still high pressure effluent of the low temperature separation zone flows into a pressure swing adsorption zone.

Selectively permeable membranes are described in U.S. Pat. Nos. 4,180,388, 4,264,338, and 4,548,619. These references are also pertinent for their showing of various arrangements of two or more membrane separation units in various series flow with recycle and interstage compression.

As mentioned previously, the two discrete catalysts of the instant invention may be located throughout the reaction zone in a uniform admixture, in separate discrete beds, or in a combination of both methods. It is also anticipated that the ZSM-5 component and the catalytically active component of lesser acidity of the second discrete catalyst which is not a ZSM-5 component may be located within the same catalyst particle. It is expected that a reactor containing catalyst particles comprised of both a ZSM-5 zeolite component and a catalytically active component of lesser acidity than the ZSM-5 component will perform similarly to a reactor system containing an intimate admixture of the two hereinabove described discrete catalysts in the dehydrocyclodimerization of a $C_2$-$C_6$ aliphatic hydrocarbon feedstock.

It was also mentioned previously that a Group IIB-IVB metal may be a component of one or both of the discrete catalysts of the instant invention. The groups set forth above are in accordance with the 1970 IUPAC Inorganic Nomenclature Rules regarding the Periodic Table of the Elements. A list of the Group IIB-IVB metals pertinent to the instant invention includes Zn, Ga, Ge, Cd, In, Sn, Tl, Pb, and Hg.

The following examples will serve to illustrate certain specific embodiments of the herein disclosed invention. These examples should not, however, be construed as limiting the scope of the invention as set forth in the claims as there are many variations which may be made thereon without departing from the spirit of the invention, as those of skill in the art will recognize.

BRIEF DESCRIPTION OF THE DRAWING

The attached FIGURE is a graphical representation of the acidity characterization of ZSM-5, mordenite, and silicalite based upon temperature programmed desorption of ammonia test results. The horizontal axis of the plot relates to acid site strength with increasing temperatures being equivalent to increasing acid strength. The vertical axis corresponds to the releative amount of acid sites of a particular strength.

EXAMPLE I

Temperature programmed desorption experiments were performed in order to determine the general acidity distribution from 25°–650° C. of powders of ZSM-5 zeolite, silicalite, and H-Mordenite.

All three powders were pretreated following the procedure below. Powder samples, each weighing 0.250 g±0.001 g, were heated at 500° C. for 75 minutes while air flowed across the sample at 60 cm$^3$/min. The samples were then heated at 500° C. for 15 minutes while helium flowed across the sample at 60 cm$^3$/min, and then allowed to cool to room temperature in a flowing helium environment. The cooled samples were then saturated with two to four 10 cm$^3$ injections of gaseous NH$_3$ and purged of excess NH$_3$ for 35 minutes with helium. The helium gas flow was then adjusted to 40 cm$^3$/min. The gas purge was then directed to a thermal conductivity cell and a programmed temperature rise was started at a rate sufficient to increase the temperature of the sample from 25°–650° C. in 75 minutes. The sample was then held at 650° C. until NH$_3$ desorption was complete.

Increasing the sample temperature causes the NH$_3$ attached to the catalytic acid sites to become desorbed. The desorbing NH$_3$ is detected by a thermal conductivity cell which is monitored along with the temperature by a recorder. An increasing desorption temperature corresponds to an increasing acid site strength of the tested powders. The thermal conductivity cell response corresponds to the number of sites of a given acid strength, and the area under the TPD curve from 25°–650° C. represents the total acidity of a given sample.

The graphical results of the temperature programmed NH$_3$ desorption tests performed on powdered samples of ZSM-5, silicalite and H-mordenite can be found in